United States Patent [19]

Greaves et al.

[11] Patent Number: 4,626,992
[45] Date of Patent: Dec. 2, 1986

[54] WATER QUALITY EARLY WARNING SYSTEM

[75] Inventors: John Greaves, Sebastopol; Robert S. Wilson, Santa Rosa; Edmund H. Smith, Sebastopol, all of Calif.

[73] Assignee: Motion Analysis Systems, Inc., Santa Rosa, Calif.

[21] Appl. No.: 612,378

[22] Filed: May 21, 1984

[51] Int. Cl.$^4$ .................. G06F 14/38; G01V 1/00; A01K 61/00
[52] U.S. Cl. ........................... 364/418; 119/3; 364/420
[58] Field of Search ............. 364/418, 420, 200, 900; 119/3, 2, 1

[56] References Cited

U.S. PATENT DOCUMENTS

| 3,929,017 | 12/1975 | Kowalski | 364/420 |
| 4,270,041 | 5/1981 | Pleyber | 235/92 T |
| 4,334,241 | 6/1982 | Kashioka | 358/107 |
| 4,392,236 | 7/1983 | Sandstrom et al. | 119/3 |

FOREIGN PATENT DOCUMENTS

| 0644424 | 1/1979 | U.S.S.R. | 119/3 |
| 0938864 | 6/1982 | U.S.S.R. | 119/3 |
| 0986368 | 1/1983 | U.S.S.R. | 119/3 |
| 1009362 | 4/1983 | U.S.S.R. | 119/3 |
| 1043696 | 9/1983 | U.S.S.R. | 119/3 |
| 1056054 | 11/1983 | U.S.S.R. | 119/3 |
| 1109102 | 8/1984 | U.S.S.R. | 119/3 |

OTHER PUBLICATIONS van der Schalie, "Utilization of Aquatic Organisms for Continuously Monitoring the Toxicity of Industrial Waste Effluents", *Technical Defense Information Center*, p. 22 (1981).
Lubinski, "Microprocessor-Based Interface Converts Video Signals for Object Tracking", *Computer Design*, pp. 81-87 (12/77).
Lubinski, "Effects of Abrupt Sublethal Gradients of Ammonium Chloride on the Activity Level, Turning and Reference-Avoidance Behavior of Bluegills", *Aquatic Toxicology, ASTM STP 707 (1978)*.
Cairns, Jr., "A Comparison of Methods and Instrumentation of Biological Early Warning Systems", *Water Resources Bulletin*, vol. 16, No. 2, pp. 261-266 (Apr. 1980).
Morgan, "Biomonitoring with Fish: An Aid to Industrial Effluent and Surface Water Quality Control", *Prog. Wat. Tech.*, vol. 9, pp. 703-711, Pergamon Press (1977).
Kleerekoper, "Some Monitoring and Analytical Techniques for the Study of Locomotor Responses of Fishes to Environmental Variables", ASTM STP 607, pp. 110-120 (1977).
Poels, "An Automatic System for Rapid Detection of Acute High Concentrations of Toxic Substances in Surface Water Using Trout, ASTM STP 607, pp. 85-95 (1977).

*Primary Examiner*—Jerry Smith
*Assistant Examiner*—Jon D. Grossman
*Attorney, Agent, or Firm*—Flehr, Hohbach, Test, Albritton & Herbert

[57] ABSTRACT

A water quality monitoring system for detecting sublethal degradations in environmental quality. The system continuously or periodically monitors the movements of a plurality of living organisms which are exposed to water from one or more selected sources. A computer controls and coordinates the tasks performed by the system. A video camera is used to visually monitor the movements of the organisms. Sensors measure other selected characteristics of the organisms' environment, including the temperature of the water. The computer includes software, responsive to the measurements by the sensors, for deriving a set of prediction parameters corresponding to the statistical distribution of expected movement patterns of the organisms. Other software is used for analyzing the organisms' movements and for comparing the observed movements with the set of prediction parameters, and for initiating the generation of a warning message when the organisms' observed movements do not correspond to the prediction parameters.

18 Claims, 4 Drawing Figures

FIG.—4

WATER QUALITY EARLY WARNING SYSTEM

The present invention relates generally to water quality monitoring systems and particularly to a system which automatically monitors the movements of living organisms which are exposed to water from the water system being monitored, determines by analyzing those movements when a potentially serious degradation in water quality has occurred, and responsively generates a warning. The present invention also relates to air quality monitoring systems using a similar method of monitoring the movements of living organisms.

BACKGROUND OF THE INVENTION

Most prior art water quality monitoring systems rely on discrete field sampling followed by laboratory analysis. Frequent chemical testing is expensive. Continuous chemical monitoring systems have not been developed because of the need for expensive, sophisticated instrumentation and highly skilled technicians to operate, calibrate and maintain the system. Furthermore chemical testing is limited by the specificity of the parameters being tested.

On the other hand, monitoring properly selected living organisms which are exposed to the water being monitored automatically detects a wide range of conditions which affect water quality. Such testing is not limited by the specification of a preselected set of parameters to be tested, because any pollutant or environmental condition which causes the organisms to move abnormally will be detected. Also such testing automatically yields an indication of the level of significance of an environmental perturbation in the form of the degree of abnormality of the organisms' movements. Dead organisms clearly indicate a more severe condition than mildly excited or mildly sluggish organisms.

While there is currently no commercial product available that continuously monitors water quality, the relevant literature describes a variety of experimental systems which monitor living organisms in order to monitor water quality. The most relevant literature is as follows: W. H. van der Schalie, Utilization of Aquatic Organisms for Continuously Monitoring the Toxicity of Industrial Waste Effluents, paper no. 22, Technical Defense Information Center 5100.36 (1981); K. S. Lubinski, et al., Microprocessor-Based Interface Converts Video Signals for Object Tracking, Computer Design, pp 81-87 (December 1977); K. S. Lubinski, et al., Effects of Abrupt Sublethal Gradients of Ammonium Chloride on the Activity Level, Turning, and Preference-Avoidance Behavior of Bluegills, Aquatic Toxicology, ASTM STP 707, pp 328-340 (1978); J. Cairns, Jr., et al., A Comparison of Methods and Instrumentation of Biological Early Warning Systems, Water Resources Bulletin, vol 16, no. 2, pp 261-266 (April 1980); W. S. G. Morgan, Biomonitoring with Fish: an Aid to Industrial Effluent and Surface Water Quality Control, Prog. Wat. Tech., vol 9, pp 703-711, Pergamon Press (1977); H. Kleerekoper, Some Monitoring and Analytical Techniques for the Study of Locomotor Responses of Fish to Environmental Variables, Biological Monitoring of Water and Effluent Quality, ASTM STP 607, pp 110-120 (1977); and C. L. M. Poels, An Automatic System for Rapid Detection of Acute High Concentrations of Toxic Substances in Surface Water Using Trout, Biological Monitoring of Water and Effluent Quality, ASTM STP 607, pp 85-95 (1977). Note that "ASTM" is an abbreviation for American Society for Testing and Materials, and "STP" is an abbreviation for Special Technical Publication.

All but one of the systems described in the literature and known to the inventors use non-video techniques for monitoring a living organism. See above cited articles by K. S. Lubinski. Most systems monitor either the breathing response of fish or use photocells to monitor their ability to maintain their position in a flowing stream of water. Video-based monitoring systems, however, have numerous advantages over types of known monitoring systems, once the problems associated with handling the large quantities of video data that are generated by a video camera have been surmounted.

All the known prior art systems monitor the health of a single fish per tank. This tends to make the system highly susceptible to idiosyncratic behavior by a single relatively intelligent organism. It also makes the system dependent on a small statistical base. But most importantly, these prior art systems could not measure interactions between organisms. The inventors have discovered that interactions between organisms, such as schooling behavior, are in some instances more sensitive to stress that other observables.

Similarly, all known prior art systems used large test organisms (i.e., fish). In most cases, the prior art system measured electrical impulses generated by the breathing of the test organisms. The need for electrical signals greater than the background noise dictated the use of large test organisms. Also, these prior art systems generally measured only one parameter, such as breathing rate, which greatly limited the ability of the system to detect stress.

It is therefore an object of the invention to provide an improved water quality early warning system which uses video techniques to monitor the movements of a plurality of living organisms.

Another object of the invention is to provide a system capable of continually or periodically monitoring water quality.

Another object of the invention is to provide a system which accommodates normal seasonal variations in water quality and normal cyclical changes in animal behavior.

Yet another object of the invention is to provide a reliable system which is basically self-operating, requires only occasional periodic maintenance, and can be produced at a low enough cost to make its use in most drinking water supply systems for medium or large populations financially justifiable.

Still another object of the invention is to provide a system which automatically updates its knowledge base and refines a comparative behavior model.

SUMMARY OF THE INVENTION

In summary the invention is a water quality monitoring system for detecting sublethal degradations in environmental quality. The system continuously or periodically monitors the movements of a plurality of living organisms which are exposed to water from one or more selected sources. A computer controls and coordinates the tasks performed by the system. A video camera is used to visually monitor the movements of the organisms. Sensors measure other selected characteristics of the organisms' environment, including the temperature of the water. The computer includes software, responsive to the measurements by the sensors, for deriving a set of prediction parameters corresponding to the statistical distribution of expected movement patterns of the organisms. Other software is used for analyzing the organisms' movements and for comparing the observed movements with the set of prediction parameters, and for initiating the generation of a warning message when the organisms' observed movements do not correspond to the prediction parameters.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENT

Figure 1:
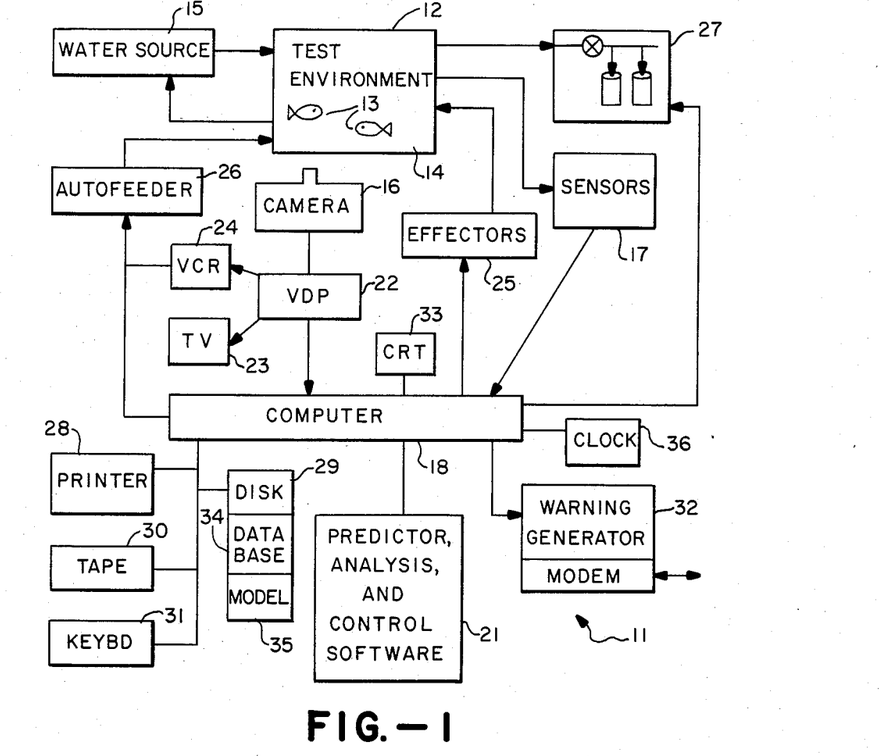
FIG. 1 depicts a block diagram of a water quality early warning system in accordance with the invention.

Referring to FIG. 1, a preferred embodiment of a water quality monitor system 11 in accordance with the invention uses a tank 12 or similar enclosure for exposing a plurality of living organisms 13 to water 14 from one or more selected water sources 15. The movements of the organisms 13 are monitored or observed by a video camera 16. Sensors 17 measure selected characteristics of the water 14 such as its temperature, dissolved oxygen, conductivity, ammonia content, hardness, turbidity, and alkalinity.

A computer 18 controls and coordinates the tasks of the system 11. In particular the computer 18 periodically initiates an observation protocol, causing observations of the organisms' movements and the water's state to be recorded. Then the recorded observations are analyzed.

The analysis by the computer 18 is basically a three step process. First, based on the historical database 34 of the organisms' movements, the observed physical variables, and the date and time of observation, it predicts the behavior of the organisms 13. Second, it analyzes the observed movements of the organisms. And third, it compares the observed movements with the predicted movements. If the observed movements differ from the predicted movements by a significant amount, a warning is generated.

The computer 18 uses predictor, analysis and control software 21 for carrying out these tasks. The predictor software, as its name indicates, is used for predicting the statistical distributions of expected movement patterns of the organisms 13. These statistical distributions of expected movement patterns are determined by a model 35 of the behavior of the organisms and are generally functions of at least some of the measured characteristics of the water's state. For example, the rapidity of the organisms' expected movements may be dependent on the water's temperature. Since the behavior or organisms is often highly rhythmic, exhibiting substantial daily, monthly, and seasonal periodicity, these statistical distributions are also functions of time and date.

The analysis software analyzes the video data produced by the video camera 16 and a video-to-digital processor (VDP) 22. The video camera 16 is a standard raster scan video camera. The VDP 22 translates the video data into a set of data representing only the outlines of all the organisms observed by the camera 16. A suitable VDP is described in U.S. patent application Ser. No. 598,827, filed on Apr. 10, 1984, entitled QUAD-EDGE VIDEO SIGNAL DETECTOR, in the names of John O. B. Greaves and David Warrender, and assigned to the same assignee as this invention. Said patent application is herein incorporated by reference.

Generally, the VDP 22 is used to filter out all the video data except data representing the time varying positions, shapes and orientations of the organisms 13. Also, while the camera 16 generally scans 60 frames per second, less frequent observations may be sufficient for purposes of the early warning system 11, depending on the speed of the organisms used. The VDP 22 can be used to select the number of frames of data per second to be used by the analysis software. In the preferred embodiment any number of frames per second can be accommodated because the number of frames per second used is a parameter used by the analysis software. The rate should generally be selected so that all significant features of the organisms' movements are observed. However it is also desirable to keep the rate as low as is practical in order to reduce the data processing load of the computer 18 and thus to minimize the cost of the computer needed to be able to handle the analysis tasks in an acceptable amount of time. In embodiments using fish as the test organisms, 15 to 30 frames per second has been found to be sufficient to observe all significant movements.

The output of the VDP 22 can be viewed on a television monitor (TV) 23 and the unprocessed picture can be recorded on video tape by a video cassette recorder 24.

The environment in the tank 12 can be affected through the use of effectors 25, such as lights, noise, agitation, as so on. A special effector is an autofeeder 26, which is used to periodically feed the organisms 13. In the preferred embodiment, feeding is controlled by the computer 18 and is coordinated with the testing of the organisms' movements.

Samples of the water being monitored can be taken for further analysis (e.g., chemical testing) by a sample taking mechanism 27, under control of the computer 18.

The computer 18 has standard peripheral devices such as a printer 28, disk drives 29, tape drive 30, CRT 33 and keyboard 31 for logging observation and test records, and other standard computer functions. In the preferred embodiment, the disk 29 stores the historical database 34 of previously observed movements by test organisms and stores one or more models 35 for use in predicting the movement of the test organisms 13. A clock 36 provides the computer 18 with the time and date.

Figure 2:
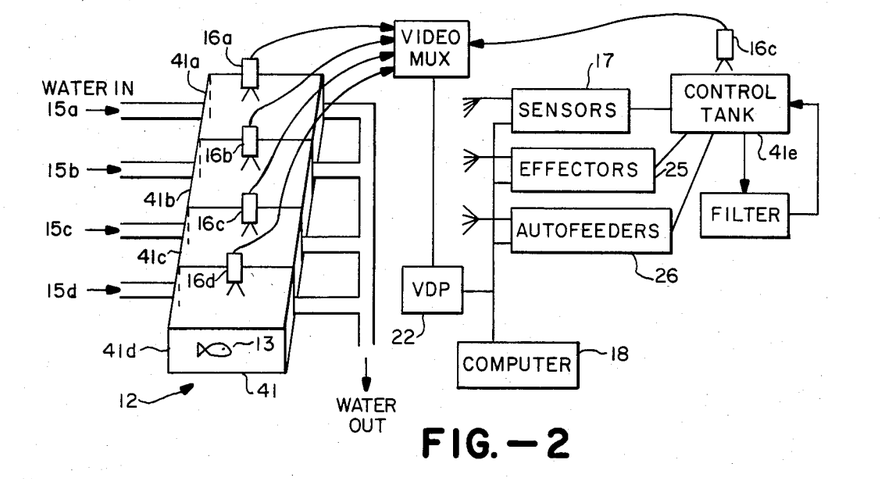
FIG. 2 depicts a block diagram of multi-tank embodiment of the invention.

Referring to FIG. 2, the test environment 12 may include several tanks 41a–41d and a control tank 41e. Each tank 41 may contain different species of test organisms 13, or may be used to test water from a different water source or from a different portion of a selected water source 15. The control tank 41e is used for exposing test organisms to water of known quality and for comparing the movements of these test organisms with the movements of the test organisms in the other tanks 41a–41d. Eventually, as the data base matures, the need for a control tank decreases. Also, some embodiments may not use a control tank due to inherent water quality control problems with closed control systems.

In multiple tank embodiments of the system 11, each tank 41 will have at least one living test organism (but usually each will have multiple subjects), a set of sensors 17 with which to monitor background environmental conditions or variables, and a video camera 16a-e with which to monitor the behavior of the test organisms 13. Generally, it is highly preferred to have multiple test subjects in each tank 41. In addition, each tank 41 generally will have effectors 25 with which to perform tasks such as impounding samples of the test medium (usually water) for subsequent chemical analysis and presenting the test organisms 13 with programmed stimuli.

Species selection for test organisms is a function of several criteria. Ideally, the test organisms should be small in size and active, consistent swimmers. They should be sensitive to a wide range of toxicants and should be easy to culture and maintain. If possible, it would be best to select organisms that have an existing data base of information on their response to a variety of toxic substances. In particular, it is noted that fish may not be the ideal test organisms, although they have been the test organisms in most prior art experimental systems. Also, using two or more species of test organisms can substantially improve the early warning system by increasing the variety of toxicants which the test organisms are sensitive to, by increasing the sensitivity to a given toxin, and by increasing the statistical base upon which the system's analyses are based.

For any one water source 15 being monitored, it may be necessary or advisable to use multiple inlets from a variety of locations. For instance, if the water source is a moving stream, it might be advisable to have one inlet near the surface for sampling floating toxicants, and one inlet at an intermediate depth. The system could be further improved by using another inlet near the bottom for sampling heavy toxicants, and a variety of other inlets at various locations (e.g., near effluent outlets, near a marina, or near either bank of the stream) for sampling potentially significantly different local water conditions.

A behavioral model 35 comprises a numerical data structure. It embodies the dependence of previously observed behavior, as recorded in a historical database 34, upon environmental state and upon time. When environmental state and time are specified, a mathematical prediction algorithm can evaluate a model so as to yield a set of prediction parameters. These prediction parameters correspond to expected statistical distributions of behavioral variables and jointly characterize an expected pattern of movement. The expected behavior resembles behavior observed under similar environmental conditions, at similar phases within various biological rhythms when the subjects were free from extreme environmental and/or biological stress.

The background environmental conditions which are used as factors in the model will depend on the particular test organisms being used. They may also depend on the particular water source being monitored. Typically, the background environmental factors will be selected from a set including temperature, dissolved oxygen, conductivity, ammonia content, hardness, turbidity, and alkalinity. Other background factors such as the brightness of the light in the test environment and barometric pressure may be used as the particular circumstances warrant. In general, the background factors will usually be conditions that can be readily tested or measured using highly reliable, automatic equipment on a frequent periodic basis.

The model may also reference a data base of previously observed movement patterns which do not conform to the basic mathematical model but which are nevertheless not indicative of the presence of significant pollution. This type of experiential data base enables automatic minor refinement of the model without having to rewrite any of the software involved. It is also essential to the formulation of new models by the robot and human behavioral scientists.

Figure 3:
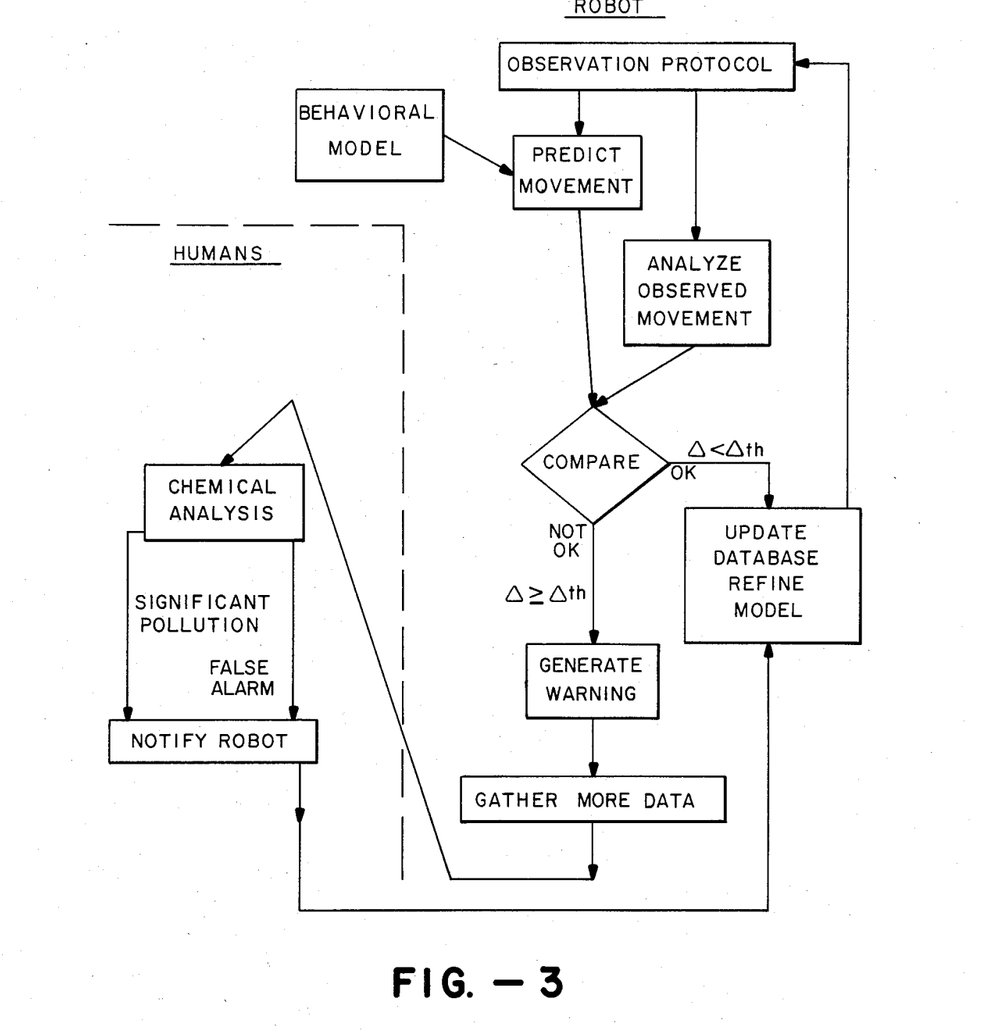
FIG. 3 depicts a flow chart of the method of the invention.

Referring now to FIG. 3, the method of the invention is divided into tasks to be performed by the system 11, denoted as a "robot" (the system 11 may be thought of as a robot behavioral scientist), and tasks to be performed by the the human behavioral scientist and the caretakers of the system 11 and the water source 15. Given a model of the expected behavior of the test organisms, the robot automatically monitors the quality of the water system 15 and warns a human caretaker when it suspects that significant pollution of the water system has occurred and therefore further testing of the water is warranted.

The basic steps of the robot biologist's process are: (1) following an observation protocol to accumulate environmental and behavioral data to be analyzed; (2) predicting the test organisms' movement patterns; (3) analyzing the observed movements of the test organisms; (4) comparing the observed movements of the test organisms with the predicted movement patterns and determining which differences, if any, are significant; and (5) refining the model if the behavior is expected. If the differences between the predicted and observed movements are significant, the process continues with: (6) generating a warning; and (7) gathering more data for analysis. If and when a warning is generated, the caretakers will normally undertake a chemical analysis of the water source. If significant pollution is detected, the robot behavior scientist 11 is allowed to continue operating. If the warning was a "false alarm" (i.e., no significant pollution was detected) the behavioral model for the test organisms is revised so that similar circumstances will not generate false alarms in the future. As discussed below, the model revision process may be either automatic (i.e., performed pursuant to predefined software routines) or manual (e.g., changes made by the human behavioral scientists to the structure of the model in order to accommodate a new input parameter or theory which affects the model in a more fundamental way than merely refining the parameter values stored in the model's data structure).

Figure 4:
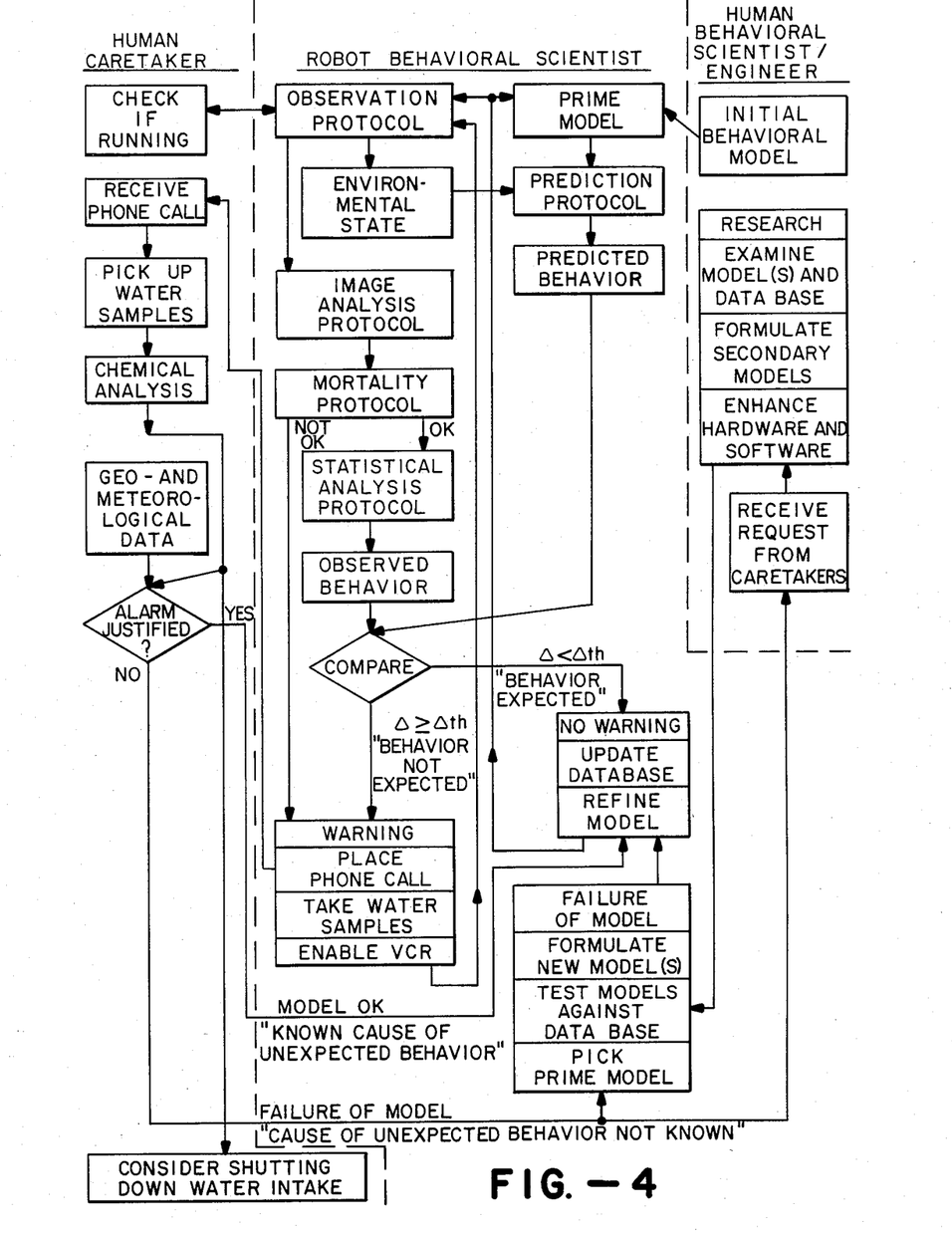
FIG. 4 depicts a more detailed flow chart of one example of the method of the invention.

Referring now to both FIGS. 3 and 4, the observation protocol in the preferred embodiment calls for periodically, once each half-hour, measuring the background environmental conditions and observing the test organisms' movements for about one minute. At various preselected times during the day, the observation protocol includes use of the autofeeder 26 and effectors 25 to feed the test organisms 13 and to vary the lighting (normally in a manner related to a natural daylight period) in the test environment 12. Each act of observation results in the production of two files of data: an environmental data file, and a video data file.

In embodiments of the system which have multiple tanks 41a-e, there may be a distinct observation protocol for each tank 41. In the preferred embodiment, each observation protocol consists of a list of commands from a "real time control command library" which comprises part of the computer's control software package 21. The initiation of each observation protocol may be controlled by a master scheduler in the computer's control software, or may be self-timed.

For each tank 41 there is a corresponding image processing protocol which specifies the analysis of the current observations and yields a specified set of behavioral variables for each test organism 13. As a preliminary step in analyzing the observed movements of the test organisms, the analysis software reduces the video data from the last observational protocol (representing the outlines of the organisms) to data representing the centroids and the orientation of the organisms. The movements of these centroids are then analyzed in a variety of ways, whereby values for a set of behavioral variables are derived. In the preferred embodiment, the primary task of the image processing protocol is to compute a time series of behavioral variables based on the original video data. Then a "mortality protocol" is executed in order to ascertain whether one (or more) of the test organisms has died. This is generally an nonlinear discriminant function of the behavioral variables. If the number of mortalities exceed a previously specified threshold, then a warning posture is adopted (i.e., a warning is issued). Otherwise the system 11 goes on to evaluate possible sublethal modifications of behavior.

The next step of the water quality monitoring method is to predict the movements of the test organisms 13 on the basis of the observed environmental variables and the time of observation. As already discussed above, predicting the movements of the test organisms 13 comprises the use of a behavioral model to calculate a set of prediction parameters which correspond to the set of expected movement patterns. The prediction process generally yields multiple statistical predictions, which specify the statistical distribution of expected movement patterns.

The set of movement parameters used to evaluate the behavior of the test organisms is selected from a set of movement analysis routines in a movement analysis library in the system's software 21. These parameters will generally include measurements such as the total distance moved during the observation period; the ratio of net distance moved to total distance moved; angular movement; speed of travel; the orientation of the organisms with respect to incoming water; positions of the organisms in the tank 41; and statistical distributions of these parameters among the observed organisms 13. These characteristics are selected both on the basis of predictability and sensitivity to perturbation by pollution. The robot behavioral scientists is programmed to automatically select and give a higher weight to the measures that are the most sensitive and predictable. These weightings will be different for different species of organisms.

After the prediction process, the system 11 follows a statistical analysis protocol which specifies the analysis of observed behavioral variables (which are derived from the video data) in terms of estimated statistical distributions and their parameters. A given statistical description protocol consists of a list of statistical commands. These statistics constitute system "observables" which are to be compared with the aforementioned prediction parameters.

After the observed movements have been characterized, the calculated system "observables" are compared with the prediction parameters by means of standard (and usually nonparametric) statistical tests. The primary result of each test is a significance level of the difference, if any, between observation and the corresponding prediction. The full gauntlet of such tests to which the observation data is subjected is collectively called a testing protocol.

Testing of the observation data can also be seen as testing of the behavioral model. From this viewpoint, a given prediction is rejected if the corresponding significance level falls below some critical level of acceptance, which may be a globle parameter within the system 11. A given model is rejected if more than a critical number (or frequency) of its predictions are rejected. The model is then said to have failed; otherwise it has succeeded. Other well known methods of specifying the criteria for determining when a deviation of observed movements from the predicted movements is significant could be employed in other embodiments of the system 11.

The system can contain a plurality of models. One model is selected as the prime model and is used for the initial analysis of the system observables. However, other models can be tested under specified conditions.

If the observed movements are not significantly different from the predicted movements (i.e., if the model succeeded for the current set of movement observations), then no warning need be generated and the system is done with the current test iteration. If, however, the observed movements are significantly different from the predicted movements (i.e., if the model "failed" or the organisms are stressed), then a warning posture is adopted by the system 11.

In the preferred embodiment, the system 11 control program can be instructed to avoid false alarms by reacting to the adoption of a warning posture by conducting more tests before generating a warning message. In other embodiments a warning message is generated immediately upon the failure of the model and then the system 11 goes about gathering more data.

In the preferred embodiment, after a warning posture is adopted, the system 11 impounds water samples, records video sequences on a VCR 24, and increases the frequency of its tests. If the subsequent tests (after the test which caused the warning posture to be adopted) conform to the model, then the incident is logged by the system for later study and possible modification of the model, and the warning posture is dropped. Only after a specified number of repeated failures of the model, and/or a specified number of multiple warnings for different test organisms in different tanks, is a full warning state adopted. A state of full warning causes the system 11 to generate a warning message.

A warning is generated normally by either placing a telephone call and/or by sending a message to another computer at a remote location. Either way, the purpose is to warn the caretakers of the water source 15 that there may be a significant pollution problem in their water supply. A telephone message is generated by using a standard electronic telephone line dialer to call a predefined telephone number and by using a standard speech synthesizer to generate a message that is transmitted to the receiver of the telephone call. In the preferred embodiment, the system 11 continues to send a warning message to a remote computer (using a standard modem) until it receives acknowledgement of its warning message. Furthermore a red warning light is activated at the site of the system 11 until the observed movements of the organisms once again conforms to the predicted range of movements.

Eventually, a human must judge whether or not a warning was justified. This judgment can be communicated the robot behavioral scientist 11 by means of the system's keyboard 31 or remotely from a computer terminal or host computer. If the warning was not justified, the robot is programmed to modify its model(s) and/or to enter the characteristics of the incident into a data base of exceptions to the model (i.e., so that the model now accepts the observed behavior as normal). Reasonable justification for a warning would include the results of chemical analysis showing obvious degradation of water quality, illness and/or parasitism of the test organisms 13, unusual meteorological and geological events, etc.

Upon performing the chemical analysis, the caretakers of the water source 15 may consider shutting down the water intake from the water source 15 to the local drinking water processing plate if the water is polluted. As confidence in the early warning system 11 increases, this decision can follow directly from the receipt of a warning message from the system 11 rather than waiting for the chemical analysis to be completed.

A model is judged to have "failed" if a warning was issued (due to deviation of its predictions from the observations) and the human behavioral scientist decides that the warning was not justified. A prime model which has failed must be replaced by another model. The new model may be a secondary model previously stored in memory. As illustrated in FIG. 4, a human behavioral scientist/engineer may provide new models. Moreover, the robot behavioral scientist may itself originate new models under software control.

An expert system, embodying heuristics for the generation of behavioral hypotheses, may generate nontrivial models capable of accounting for the previous history of the organisms' behavior. Naturally, a good model must also successfully discriminate between healthy and not healthy behavior. Therefore the model must not trivially cover the observed system's history, for example through the use of a many-ordered polynomial function fitted to past data points, or through non-meaningful criteria such as a requirement that the test organisms move slower than the speed of light.

Generally, the robot behavioral scientist will have access to multiple models (some of its own devising and some entered by a human) and must select one of these as the next prime model upon which its predictions are to be based. The model chosen as the prime model is the one which best accounts for the previous history of the organisms' behavior. This history has been encoded in a database or knowledge base and includes a representation of observed behavior which triggered the failure of the previous model. Just as a working prime model is tested by its (correct or faulty) anticipation of future observations (i.e., prediction), a new candidate is tested by its (correct or faulty) accord with past observations (i.e., retrodiction). The model which best "explains" past behavior is then adopted as the basis for predicting future observations.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims. In particular, the present invention applies equally well to air quality monitoring systems using a similar method of monitoring the movements of living organisms.

What is claimed is:

1. In a system for monitoring water quality in a selected water system:
   (a) tank means for exposing a plurality of living organisms to water from said selected water system;
   (b) video means for simultaneously visually monitoring the movements of a plurality of said organisms in said tank means;
   (c) sensor means for measuring selected characteristics of said organisms' environment including the temperature of said water;
   (d) warning means for generating a warning message; and
   (e) computer means, coupled to said video means, sensor means and warning means, for automatically, periodically evaluating the quality of the water in said water system, including
      video analysis means for generating a set of observed statistical distributions for a multiplicity of preselected movement parameters based on said movements of said plurality of organisms monitored by said video means;
      predictor means, responsive to measurements by said sensor means, for generating a set of prediction parameters, including
         behavioral model means for defining a set of expected statistical distributions for said multiplicity of preselected movement parameters, wherein each of a plurality of said expected statistical distributions defined by said behavioral model means is a function of one or more measurements by said sensor means, and said set of prediction parameters corresponds to said set of expected statistical distributions; and
      analysis means for analyzing said movements of said organisms monitored by said video means, including means for comparing said set of observed statistical distributions with said set of prediction parameters and for activating said warning means when said movements do not correspond to said prediction parameters.

2. A system as set forth in claim 1, further including:
   (f) autosampler means, responsive to said computer means, for retaining one or more samples of said water.

3. A system as set forth in claim 2, further including:
   (g) effector means, responsive to said computer means, for affecting selected aspects of the environment in said tank means, including autofeeder means for periodically feeding said organisms.

4. A system as set forth in claim 3, further including clock means for providing said computer means with the time of observation of said movements;
   wherein
   said predictor means is responsive to the time of observation and to changes in the environment in said tank means effected by said effector means, so that said set of prediction parameters varies in accordance with the temperature of said water, the time of observation, and changes in the environment in said tank means effected by said effector means.

5. A system as set forth in claim 4, wherein
   said warning means includes means for conveying a warning message to one or more selected remote locations.

6. A system as set forth in claim 5, wherein
said tank means includes a plurality of separate test environments.

7. A system as set forth in claim 6, wherein
said tank means includes a control environment for exposing living organisms to water of known quality and a test environment for exposing living organisms to water from said selected water system; wherein said video means include means for visually monitoring the movements of said organisms in said control environment and said computer means includes means for using said movements of said organisms in said control environment as a factor in the analysis of the movements of said organisms in said test environment.

8. A system as set forth in claim 1, further including
clock means for providing said computer means with the time of observation of said movements;
wherein
said behavioral model means includes means for quantifying expected distributions of selected behavioral variables as a function of the time of observation and of selected characteristics of said organisms' environment, and for quantifying the significance of observed behavior which deviates from said expected distribution.

9. A system as set forth in claim 8, wherein
said analysis means includes means for causing said system to adopt a warning posture when a first predefined set of tests indicates that said movements do not correspond to said prediction parameters;
said analysis means further including means for conducting a second predefined set of tests upon the adoption of a warning posture by said system, wherein a specified quantity of said second predefined set of tests must indicate that said movements do not correspond to said prediction parameters before said analysis means activates said warning means.

10. In a method of monitoring water quality in a selected water system, the steps of:
exposing a plurality of living organisms to water from said selected water system;
simultaneously visually monitoring the movements of a plurality of said organisms;
measuring selected characteristics of said organisms' environment including the temperature of said water;
providing a behavioral model for defining a set of expected statistical distributions for a multiplicity of preselected movement parameters, wherein said expected statistical distribution for parameters is a function of one or more measurements of said selected characteristics of said organisms' environment;
and for automatically, periodically performing the steps of:
gnerating a set of observed statistical distributions for said multiplicity of preselected movement parameters based on said movements of said plurality of visually monitored organisms;
in response to measurements by said sensor means, generating a set of prediction parameters corresponding to said set of expected statistical distributions;
analyzing said movements, including comparing said observed statistical distributions with said set of prediction parameters; and
generating a warning message when said movements do not correspond to said prediction parameters.

11. A method as set forth in claim 10, wherein
said exposing step includes exposing a plurality of species of living organisms to water from said selected water system in a plurality of separate test environments; and
said visually monitoring and measuring steps include observing the movements of said organisms in each of said test environments.

12. A method as set forth in claim 10,
further including the step of
keeping track of the time of observation of said movements;
wherein
said behavior model includes means for quantifying expected distributions of selected behavioral variables as functions of the time of observation and of selected characteristics of said organisms' environment, and for quantifying the significance of observed behavior which deviates from said expected distribution.

13. A method as set forth in claim 12, wherein
said analyzing step includes adopting a warning posture when a first predefined set of tests indicates that said movements do not correspond to said prediction parameters; and conducting a second predefined set of tests upon the adoption of a warning posture;
wherein a specified quantity of said second predefined set of tests must indicate that said movements do not correspond to said prediction parameters before said generating step is performed.

14. In a system for monitoring environmental quality in a selected environmental system;
(a) tank means for exposing a plurality of living organisms to an environmental medium from said selected environmental system;
(b) video means for simultaneously visually monitoring the movements of a plurality of said organisms in said tank means;
(c) sensor means for measuring selected characteristics of said organisms' environment including the temperature of said environmental medium;
(d) warning means for generating a warning message; and
(e) computer means, coupled to said video means, sensor means and warning means, for automatically, periodically evaluating the quality of the environmental medium in said environmental system, including
video analysis means for generating a set of observed statistical distributions for a multiplicity of preselected movement parameters based on said movements of said plurality of organisms monitored by said video means;
predictor means, responsive to measurements by said sensor means, for generating a set of prediction parameters, including
behavioral model means for defining a set of expected statistical distributions for said multiplicity of preselected movement parameters, wherein each of a plurality of said expected statistical distributions defined by said behavioral model means is a function of one or more measurements by said sensor means, and said set of prediction parameters corresponds to said set of expected statistical distributions; and analysis means for analyzing said movements of said organisms monitored by said video means, including means for comparing said set of observed statistical distributions with said set of prediction parameters and for activating said warning means when said movements do not correspond to said prediction parameters.

15. A system as set forth in claim 14, further including clock means for providing said computer means with the time of observation of said movements; wherein said predictor means is responsive to the time of observation and to changes in the environment in said tank means effected by said effector means, so that said set of prediction parameters varies in accordance with the temperature of said environmental medium, the time of observation, and changes in the environment in said tank means effected by said effector means.

16. A system as set forth in claim 15, wherein said environment medium is air.

17. In a method of monitoring environmental quality in a selected environmental system, the steps of:

exposing a plurality of living organisms to an environmental medium of said selected environmental system;

simultaneously visually monitoring the movements of a plurality of said organisms;

measuring selected characteristics of said organisms' environment including the temperature of said environmental medium;

providing a behavioral model for defining a set of expected statistical distributions for a multiplicity of preselected movement parameters, wherein said expected statistical distribution for parameters is a function of one or more measurements of said selected characteristics of said organisms' environment;

and for automatically, periodically performing the steps of:

generating a set of observed statistical distributions for said multiplicity of preselected movement parameters based on said movements of said plurality of visually monitored organisms;

in response to measurements by said sensor means, generating a set of prediction parameters corresponding to said set of expected statistical distributions;

analyzing said movements, including comparing said observed statistical distributions with said set of prediction parameters; and generating a warning message when said movements do not correspond to said prediction parameters.

18. A method as set forth in claim 17, further including the step of keeping track of the time of observation of said movements;

wherein said deriving step is responsive to said time of observation.

* * * * *